US010506980B2

(12) United States Patent
Oleson (10) Patent No.: US 10,506,980 B2
(45) Date of Patent: Dec. 17, 2019

(54) SCALE FOR DISPLAYING WORKOUT READINESS (71) Applicant: Under Armour, Inc., Baltimore, MD (US)

(72) Inventor: Mark A. Oleson, Baltimore, MD (US)

(73) Assignee: Under Armour, Inc., Baltimore, MD (US)

( * ) Notice: Subject to any disclaimer, the term of this patent is extended or adjusted under 35 U.S.C. 154(b) by 0 days.

(21) Appl. No.: 14/730,467

(22) Filed: Jun. 4, 2015

(65) Prior Publication Data
US 2016/0213334 A1 Jul. 28, 2016

Related U.S. Application Data (60) Provisional application No. 62/106,931, filed on Jan. 23, 2015.

(51) Int. Cl.
A61B 5/024 (2006.01)
A61B 5/00 (2006.01)

(52) U.S. Cl.
CPC ............ A61B 5/72 (2013.01); A61B 5/02405 (2013.01)

(58) Field of Classification Search
CPC ............ A63B 24/0059; A63B 24/0062; A63B 2024/0065; A63B 2024/0068; G01G 19/44; G01G 19/50; G06F 19/3431; A61B 5/02405; A61B 5/02438
See application file for complete search history.

(56) References Cited

U.S. PATENT DOCUMENTS

| 2005/0070809 | A1* | 3/2005 | Acres | A61B 5/0006 600/508 |
| 2010/0324427 | A1* | 12/2010 | Devot | A61B 5/0205 600/484 |
| 2011/0137191 | A1* | 6/2011 | Kinnunen | A61B 5/04011 600/512 |
| 2014/0005947 | A1* | 1/2014 | Jeon | G06F 19/3431 702/19 |
| 2014/0142396 | A1* | 5/2014 | Ricks | A61B 5/0537 600/301 |
| 2015/0038806 | A1* | 2/2015 | Kaleal, III | A61B 5/4872 600/301 |
| 2016/0033319 | A1* | 2/2016 | Kovacs | G01G 19/44 177/25.13 |
| 2016/0038037 | A1* | 2/2016 | Kovacs | A61B 5/0205 600/301 |
| 2016/0066835 | A1* | 3/2016 | He | A61B 5/6898 482/4 |
| 2017/0188847 | A1* | 7/2017 | Ahmed | A61B 5/02405 |

* cited by examiner

Primary Examiner — George R Evanisko
(74) Attorney, Agent, or Firm — Maginot, Moore Beck LLP (57) ABSTRACT Techniques are provided for displaying exercise information to an individual, including, for example, an exercise readiness indication. A display device receives information of a physiological measurement of a user. The display device determines if the physiological measurement falls within a predetermined range of values. The display device then displays to the user an exercise readiness indication that represents a readiness state of the user to participate in an exercise activity based on the physiological measurement.

12 Claims, 7 Drawing Sheets

SCALE FOR DISPLAYING WORKOUT READINESS

RELATED APPLICATIONS

This application claims priority from U.S. Provisional Patent Application No. 62/106,931 filed on Jan. 23, 2015, the entirety of which is incorporated by reference herein.

TECHNICAL FIELD

The present disclosure relates to techniques for determining an individual's readiness for exercise activity.

BACKGROUND OF THE INVENTION

Consistent exercise has lasting health benefits. An exerciser's performance during a workout session depends on many factors including, for example, the exerciser's base line health status, nutritional habits, athletic skill, training regiment, etc. Such factors are the subject of much research. Often, an exerciser's physiological state may affect the quality and duration of an exercise or athletic performance event. Ideally, an exerciser would perform a workout at a time that optimizes his or her mental and physical state.

DETAILED DESCRIPTION OF EXAMPLE EMBODIMENTS

Overview

Techniques are provided for displaying exercise information to an individual, including, for example, an exercise readiness indication. A display device receives information of a physiological measurement of a user. The display device determines if the physiological measurement falls within a predetermined range of values. The display device then displays to the user an exercise readiness indication that represents a readiness state of the user to participate in an exercise activity based on the physiological measurement.

Example Embodiments

The techniques described herein relate to displaying exercise information to an individual, including, for example, an exercise readiness indication. An electronic device may obtain physiological measurement information from a user and upon obtaining such information may display an exercise readiness indication to the user. Such an indication improves the functioning of the device since it is able to determine and display an exercise readiness status to a user. Furthermore, devices that obtain physiological measurement information to determine exercise readiness can operate more efficiently to indicate to the user an exercise readiness.

Figure 1:
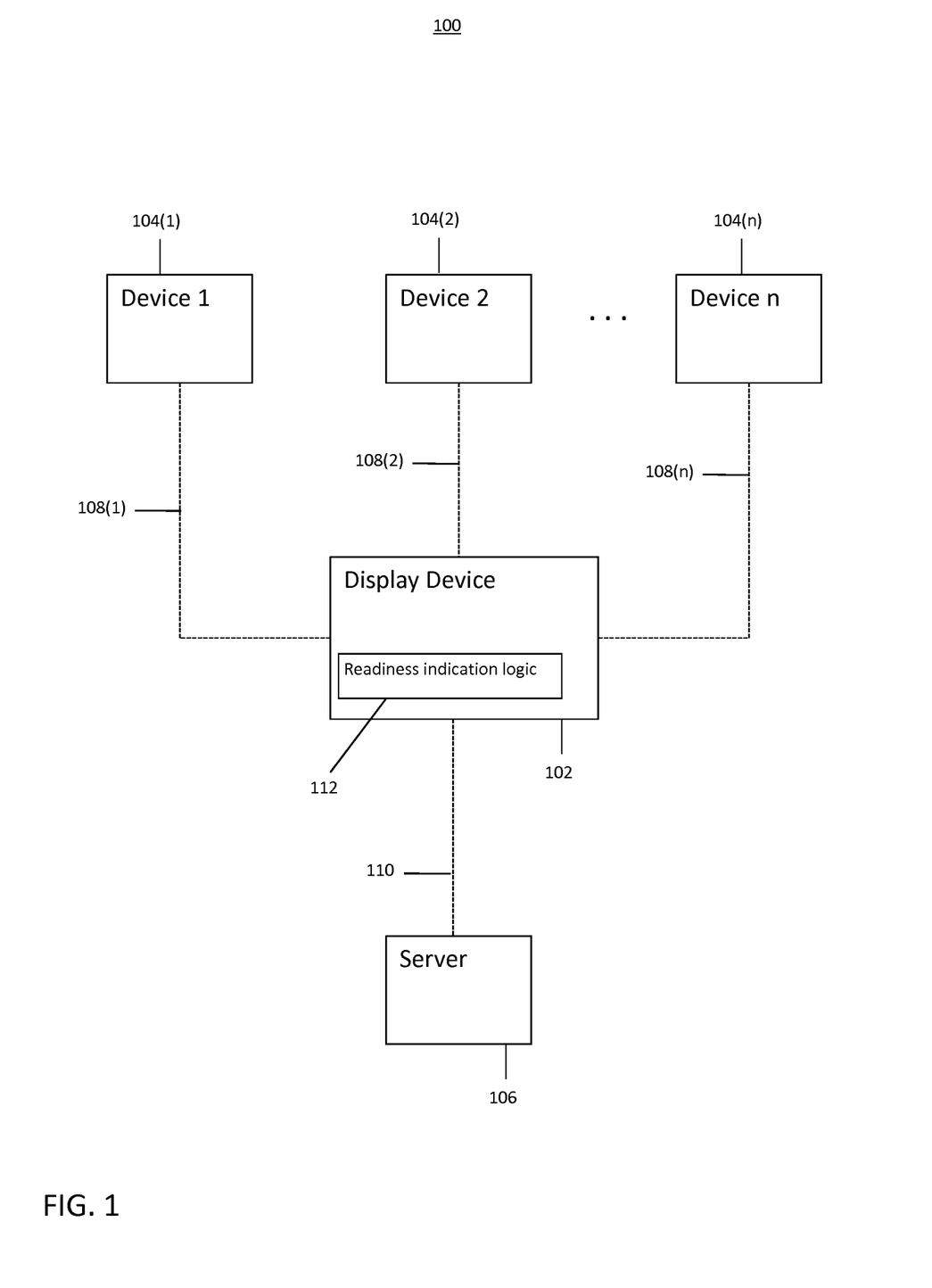
FIG. 1 shows an example system topology depicting a display device that communicates with a plurality of other devices to display an exercise readiness indication to a user.

Reference is made to FIG. 1, which shows an example system topology 100 that includes a display device 102, one or more other devices 104(1)-104(n) and a server device ("server") 106. The display device 102 is configured to communicate (e.g., wirelessly) with any one or more of the devices 104(1)-104(n) and with the server 106. The display device 102 is, for example, able to send and receive wireless communications with each of the other devices 104(1)-104(n) and the server 106. These communications may be in accordance with known or heretofore contemplated wireless protocols (e.g., Wi-Fi, Bluetooth, radio frequency, near field communication, etc.). The display device 102 may be referred to hereinafter as "display device." Likewise, device 104(1) may be referred to hereinafter as "device 1," device 104(2) may be referred to hereinafter as "device 2," and so on. The devices 104(1)-104(n) may also be referred to individually as a physiological measurement device.

In one example, the display device 102 is a scale on which an individual (also referred to hereinafter as a "user" or "exerciser") is configured to stand. As will be described in more detail herein, the scale may be configured to measure various physiological metrics of the individual, including, for example, the individual's weight, body mass index, lean mass weight and percentage, body fat weight and percentage, bone density, etc. These metrics may be measured by techniques known or heretofore contemplated. It should be appreciated that the display device 102 may be any other electronic device that is configured to obtain such physiological metrics. For simplicity and ease of explanation, the display device 102 is described hereinafter as a scale, and it may be referred to hereinafter as scale 102.

The display device 102 is configured to display physiological metrics to the individual. In addition to measuring the various physiological metrics (described above) for the individual, the display device 102 may receive from other devices physiological information of the individual. For example, the display device 102 may be configured to exchange wireless communications with one or more of the devices 104(1)-104(n). Additionally, the display device 102 may be configured to exchange wireless communications with a server 106. As described herein, the display device 102 may obtain from one or more of the devices 104(1)-104(n) and/or the server 106 physiological information (e.g., physiological measurements) of a user. One or more of the devices 104(1)-104(n) may be configured to measure and/or store various physiological metrics of the individual and may be configured to send such metrics to the display device 102. Though not shown in FIG. 1, the devices 104(1)-104(n) may themselves communicate with the server 106, and thus the physiological information of a user may be stored on the server 106 and may be accessible by the display device 102. In another example, the physiological information measured by the devices 104(1)-104(n) may be stored on the devices themselves.

The display device 102, upon receiving the physiological metrics (e.g., from one or more of the devices 104(1)-104(n) and/or the server 106), may be configured to display the physiological metrics to the individual when the individual is nearby or standing on the scale. Furthermore, the display device 102 is configured to analyze the physiological metrics received from one or more of the devices 104(1)-104(n) and/or the server 106 and to process the information of the physiological metrics to determine an exercise readiness level of an individual. These techniques are described in more detail herein.

In one example, the devices 104(1)-104(n) may be health wearable devices worn by an individual. These wearable devices are configured to measure and collect physiological and biometric data of an individual. For example, the wearable devices may be configured to monitor, measure and collect data related to an individual's step count, sleep, heart rate, heart rate variability, blood oxygen level, caloric burn, exercise data (e.g., speed, distance traveled, jump height, loft, stride length, cadence), electrocardiogram measurements, electroencephalogram measurements, muscle contraction, etc. Thus, such wearable devices may be called step count monitoring/measuring devices, sleep monitoring/measuring devices, heart rate monitoring/measuring devices, heart rate variability monitoring/measuring devices, etc. It should be appreciated that these metrics are merely examples, and that the techniques described herein are applicable for any physiological or biometric data (including those described above) of an individual capable of being measured by a wearable device. In one example, any of the devices 104(1)-104(n) may be wearable devices that are capable of being worn by or affixed to an individual, such as the individual's wrist, head, torso, leg, foot, arm, or any other portion of the individual's body. It should be appreciated that the devices 104(1)-104(n) may also be devices that measure physiological data and that are located proximate the individual but not directly affixed to the individual.

The display device 102 is in communication with the devices 104(1)-104(n), as represented by reference numerals 108(1)-108(n). Reference numeral 108(1) is representative of a wireless communication link (e.g., Wi-Fi, Bluetooth, or communications in accordance with other wireless communication protocols) between device 1 and the display device 102. Likewise, reference numeral 108(2) is representative of a wireless communication link between device 2 and the display device 102, and reference numeral 108(n) is representative of a wireless communication link between device n and the display device 102. FIG. 1 also shows link 110 that is representative of a wireless communication link between the server 106 and the display device 102. It should be appreciated that any of the 108(1)-108(n) and 110 links may alternatively be wired links. Also, it should be appreciated that the display device 102 and one or more of the devices 104(1)-104(n) and/or the server 106 may be present in the same network (e.g., a Personal Area Network (PAN), Local Area Network (LAN), Wide Area Network (WAN), etc.). Thus, each of the devices 104(1)-104(n) is able to send data, including physiological data of an individual, to the display device 102 via a respective communication link. Likewise, the server 106 is able to send data, including physiological data of an individual, to the display device 102. The display device 102, upon receiving the data from one or more of the devices 104(1)-104(n) and/or the server 106 can provide (e.g., display) to the individual an exercise readiness indication to the user to indicate to the user a readiness state of the user to participate in an exercise activity. Reference numeral 112 represents readiness indication logic that is stored on the display device 102 and executed by a processor on the display device 102 to display an exercise readiness indication to a user. These techniques are described herein.

Figure 2:
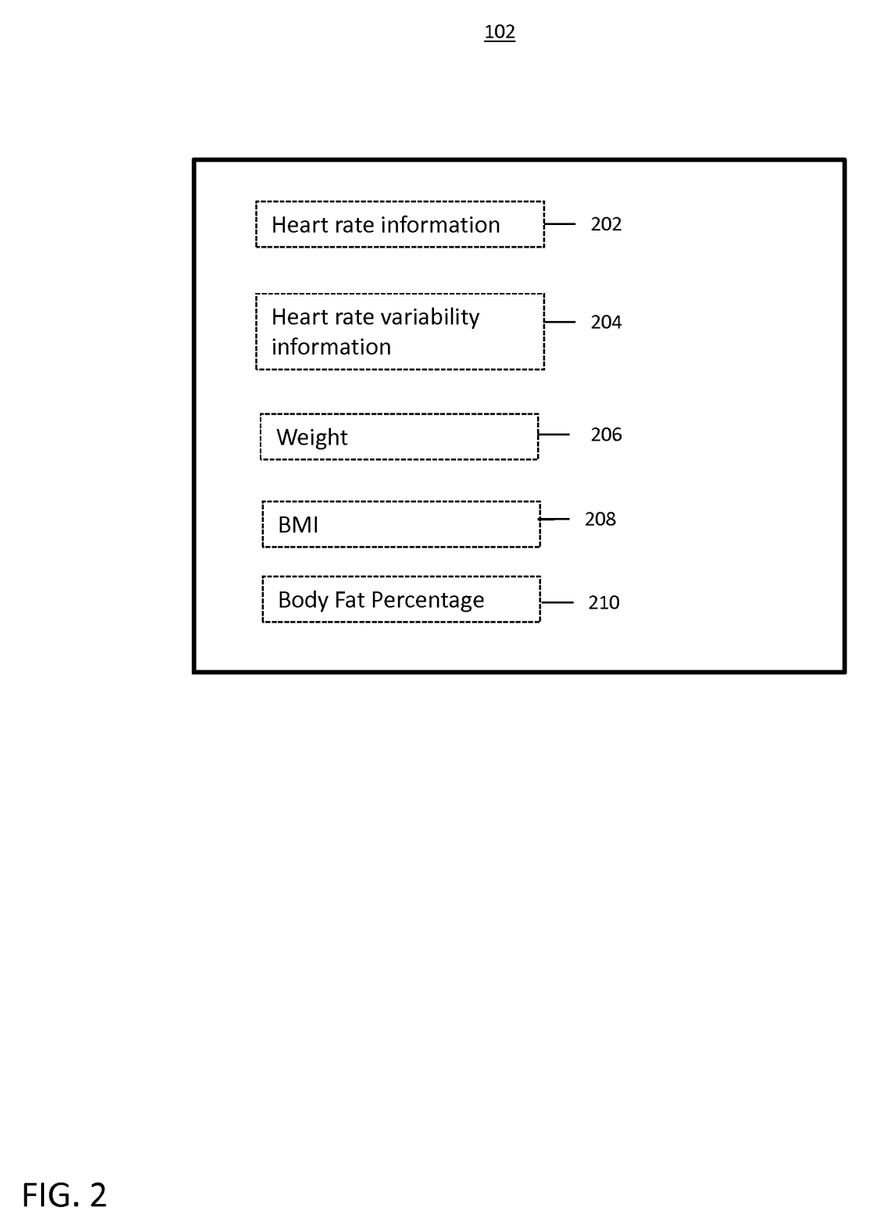
FIG. 2 shows the display device displaying physiological metrics of the user.

Reference is now made to FIG. 2, which shows the display device 102 displaying information, including physiological metrics, to the user. As stated above, the display device 102 receives physiological data from one or more of the devices 104(1)-104(n) via a respective communication link 108(1)-108(n) and/or from the server 106 via the communication link 110. In FIG. 2, the display device 102 displays to an individual the individual's heart rate and heart rate variability, weight, body mass index (BMI) and body fat percentage, as shown in reference numerals 202-210. For example, reference numeral 202 represents a display of heart rate measurement metrics of a user, reference numeral 204 represents a display of heart rate variability measurement metrics of a user, reference numeral 206 represents a display of weight information of a user, reference numeral 208 represents a display of BMI measurements of a user, and reference numeral 210 represents a display of body fat percentage measurements of a user. It should be appreciated that these are merely examples, and that the display device 102 may be configured to display other physiological measurements of a user.

In one example, the display device 102 is configured to measure the user's weight, body mass index and body fat percentage when a user steps on the scale, while obtaining the heart rate and heart rate variability In one example, the display device 102 is a scale that measures the weight, body mass index, and body fat percentage as the individual steps on the scale and obtains the heart rate, and heart rate variability information from one or more of the devices 104(1)-104(n) and/or the server 106. In another example, the display device 102 is configured to measure all of the physiological measurements of the user. In yet another example, the display device 102 is configured to receive all of the physiological measurements from one or more of the devices 104(1)-104(n) and/or the server 106. It should be appreciated that these are merely examples, and the display device 102 may be configured to measure any or all of the physiological metrics itself or may be configured to receive any or all of the physiological metrics from the devices 104(1)-104(n) and/or the server 106.

In an example embodiment, when the display device 102 receives or obtains the heart rate and heart rate variability information from one or more of the devices 104(1)-104(n) (e.g., from a heart rate monitor worn on a chest or wrist/arm of a user) or the server 106, the display device 102 displays that information to the user, along with other metrics such as weight, BMI and body fat percentage measured by the display device 102. It should be appreciated that in one example, the server 106 may receive the heart rate information and heart rate variability information from another device (e.g., device 104(1)-104(n) or some other health measurement device) and may store the information upon receipt in a database. As stated above, the display device 102 may receive the heart rate measurement metric and the heart rate variability measurement metric from one or more wearable devices via a known or heretofore contemplated wireless communication protocol.

Figure 3A:
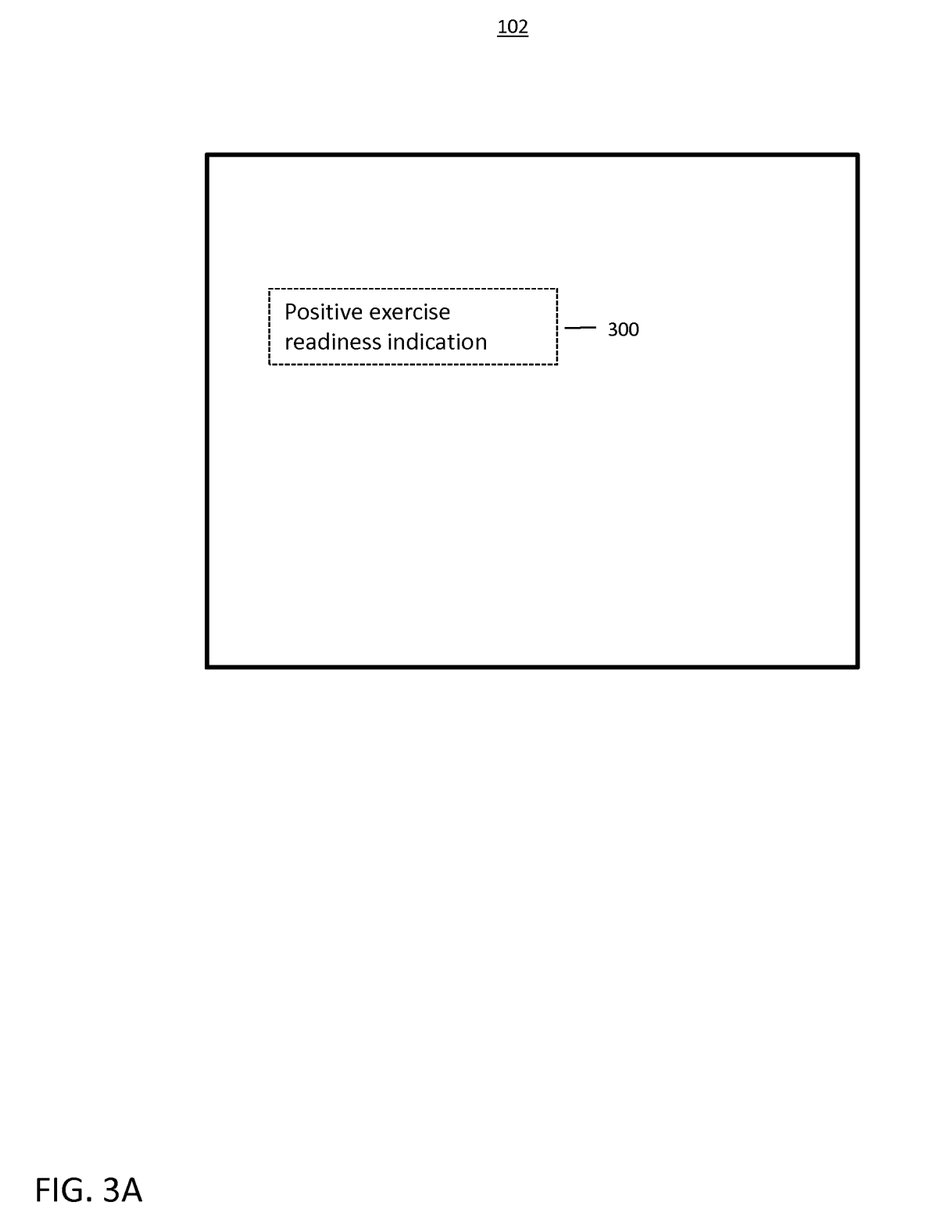
FIGS. 3A and 3B show the display device displaying the exercise readiness indication to the user.
Figure 3B:
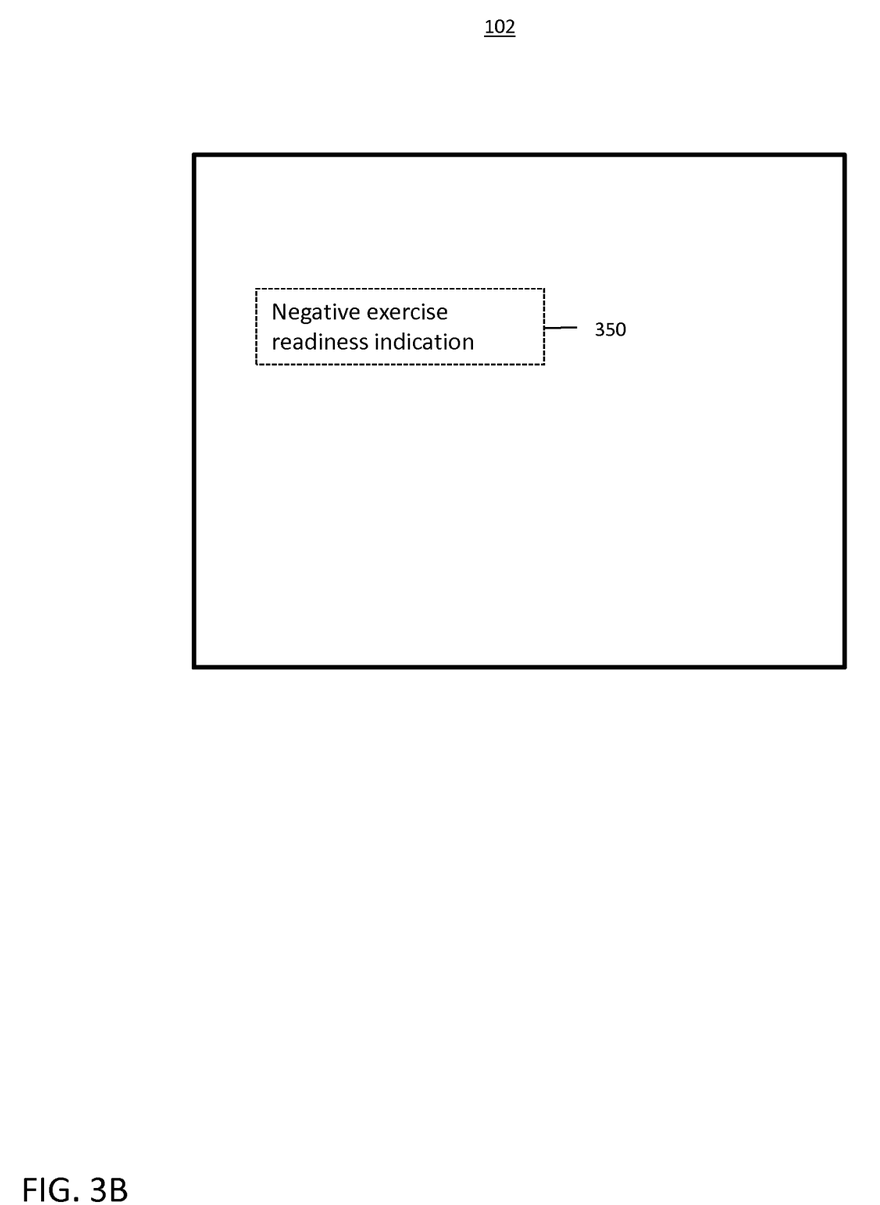

Reference is now made to FIGS. 3A and 3B. FIG. 3A shows the display device 102 in a positive readiness configuration 300, and FIG. 3B shows the display device 102 in a negative readiness configuration 350. In the example in FIGS. 3A and 3B the display device 102 receives from one or more of the devices 104(1)-104(n) and/or the server 106 heart rate and heart rate variability information of a user. Upon such receipt, the display device 102 executes an algorithm to determine whether or not the heart rate and/or heart rate variability metrics fall within a predetermined acceptable range of values. Alternatively, the display device 102 executes an algorithm to determine whether or not the heart rate and/or heart rate variability metrics each are within an upper threshold and/or lower threshold value. Based on these determinations, the display device 102 will display to the user a readiness indication. The readiness indication is a representation of a readiness state of the user to participate in an exercise activity based on the physiological measurement (e.g., heart rate and/or heart rate variability).

For example, in FIG. 3A, the display device 102 displays to the user a positive exercise readiness indication 300 to the user. The positive exercise readiness indication 300 indicates to the user that the user is in a ready state to participate in an exercise activity when the physiological measurement is within a predetermined range of values (and/or within acceptable upper or lower thresholds). For example, the display device 102 will display a positive exercise readiness indication 300 when the heart rate or heart rate variability information (e.g., received from devices 104(1)-104(n) or the server 106) is within an acceptable range of values or within an acceptable upper or lower threshold. The positive exercise readiness indication 300 may take a variety of forms. For example, the positive exercise readiness indication 300 may be a text indication provided to the user that the user is ready to perform exercise activity. The positive exercise readiness indication 300 may also be an audio output, graphical output, color output, etc. For example the display device 102 may light up with a certain color (e.g., green) and/or provide an audio output as the positive exercise readiness indication 300.

In another example, in FIG. 3B, the display device 102 displays to the user a negative exercise readiness indication 350 to the user. The negative exercise readiness indication 350 indicates to the user that the user is not in a ready state to participate in an exercise activity when the physiological measurement is not within the predetermined range of values (and/or within acceptable upper or lower thresholds). For example, the display device 102 will display a negative exercise readiness indication 350 when the heart rate or heart rate variability information is not within an acceptable range of values or not within an acceptable upper or lower threshold. The negative exercise readiness indication 350 may take a variety of forms. For example, the negative exercise readiness indication 350 may be a text indication provided to the user that the user is not ready to perform exercise activity. The negative exercise readiness indication 350 may also be an audio output, graphical output, color output, etc. For example the display device 102 may light up with a certain color (e.g., red) and/or provide an audio output as the negative exercise readiness indication 350. It should be appreciated that the negative exercise readiness indication 350 may also be an indication to the user that the user might not be in an optimal condition to perform in exercise. In other words, in one example, the negative exercise readiness indication 350 does not necessarily indicate to the user that the user is not in an exercise-ready condition. Instead, the negative exercise readiness indication 350 may indicate to the user that though the user is not in an optimal exercise-ready condition, the user may still be ready to perform an exercise. In this example, the display device 102 may display an indication (e.g., a yellow color) that is different from the indication displayed when the user is not in an exercise-ready condition.

Figure 4:
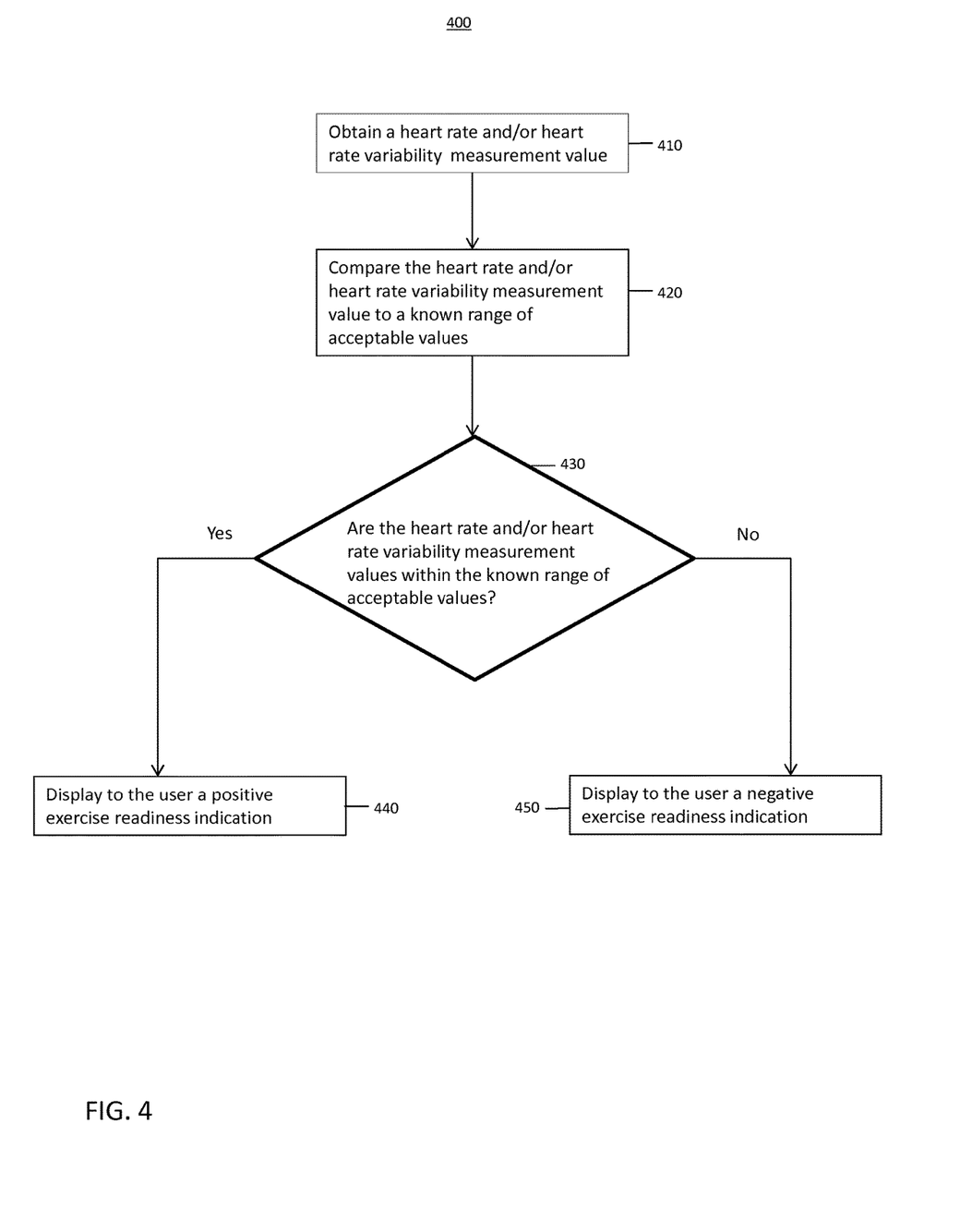
FIG. 4 shows an example flow chart depicting operations for determining to display the exercise readiness to the user.

Reference is now made to FIG. 4, which shows an example flow chart 400 depicting operations for determining and displaying the exercise readiness to the user. At operation 410, the display device 102 obtains heart rate and/or heart rate variability measurement values for a user. As described above, the display device 102 may receive these values from one or more of the devices 104(1)-104(n) and/or the server 106. Alternatively, the display device 102 may itself measure these metrics. At operation 420, the display device 102 compares the heart rate and/or heart rate variability measurement values to a known range of acceptable values. At operation 430, the display device 102 determines whether or not the heart rate and/or heart rate variability measurement values are within the known range of acceptable values. For example, a known range of acceptable values may be values that are commonly known for individuals who are healthy and who are of a variety of fitness levels (e.g., active, athletic, etc. fitness levels). The range of acceptable values may vary based upon a user's age, gender, height, medical history, predetermined/preexisting health conditions, etc. It should be appreciated that the range of acceptable values may be customized to specific users, and thus, different users may have different ranges of acceptable values. Additionally, the range of acceptable values may change based on a historical analysis of physiological information of the user. Thus, it should be appreciated that the range of acceptable values may vary and change from user to user and may change over time for particular users.

If the display device 102 determines that the heart rate and/or heart rate variability measurement values are within a known range of acceptable values, the display device 102, at operation 440, displays to the user a positive exercise readiness indication (e.g., as described in connection with FIG. 3A, above). If the display device 102 determines that the heart rate and/or heart rate variability measurement values are outside of a known range of acceptable values, the display device 102 displays to the user a negative exercise readiness indication (e.g., as described in connection with FIG. 3B, above).

Figure 5:
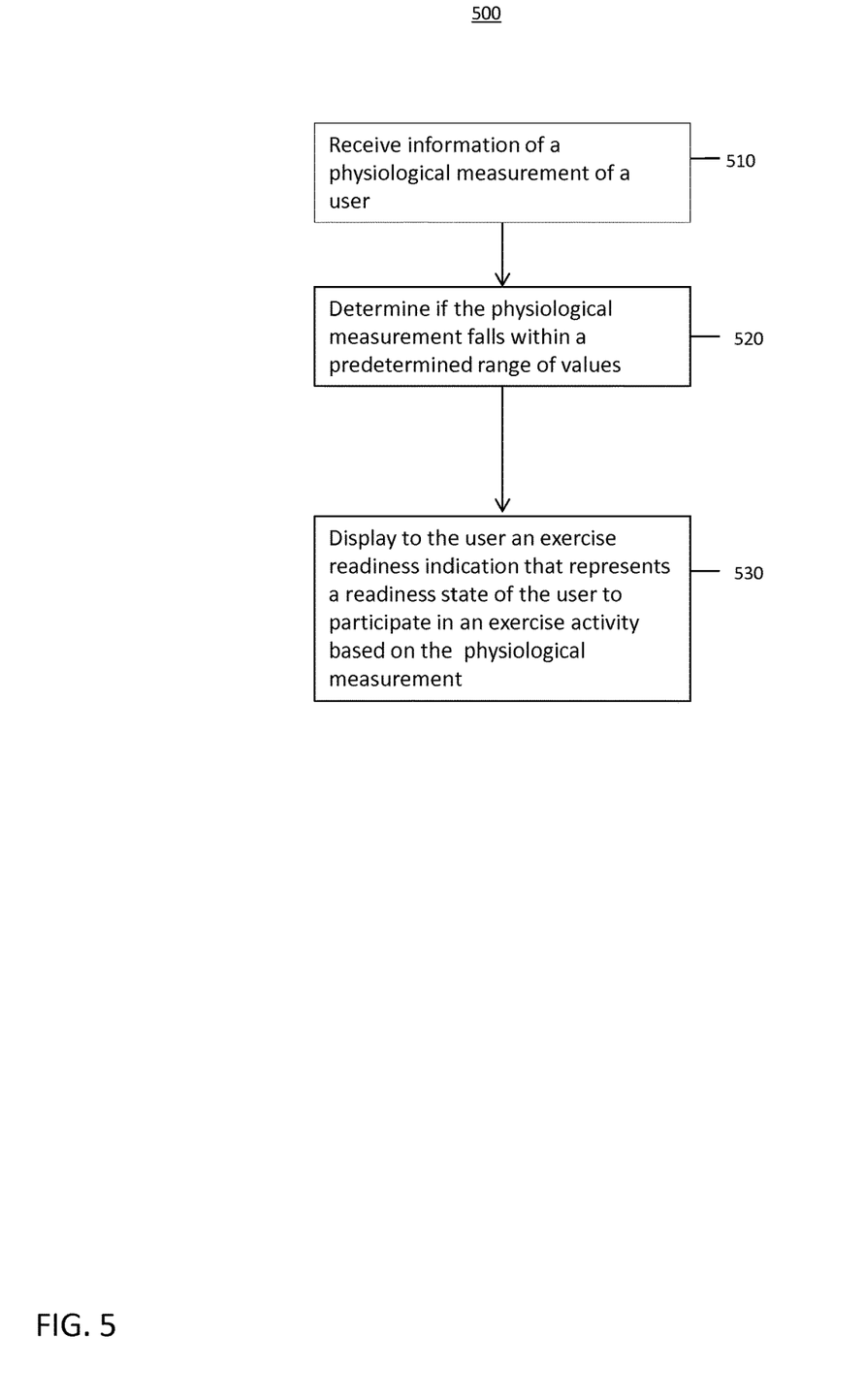
FIG. 5 shows an example flow chart depicting operation for displaying the exercise readiness to the user.

Reference is now made to FIG. 5, which shows an example flow chart 500 depicting operations of the display device 102 displaying the exercise readiness information to the user. At reference numeral 510, the display device 102 receives information of a physiological measurement of the user. At reference numeral 520, the display device 102 determines if the physiological measurement falls within a predetermined range of values. At reference numeral 530, the display device 102 displays to the user an exercise readiness indication that represents a readiness state of the user to participate in an exercise activity based on the physiological measurement.

Figure 6:
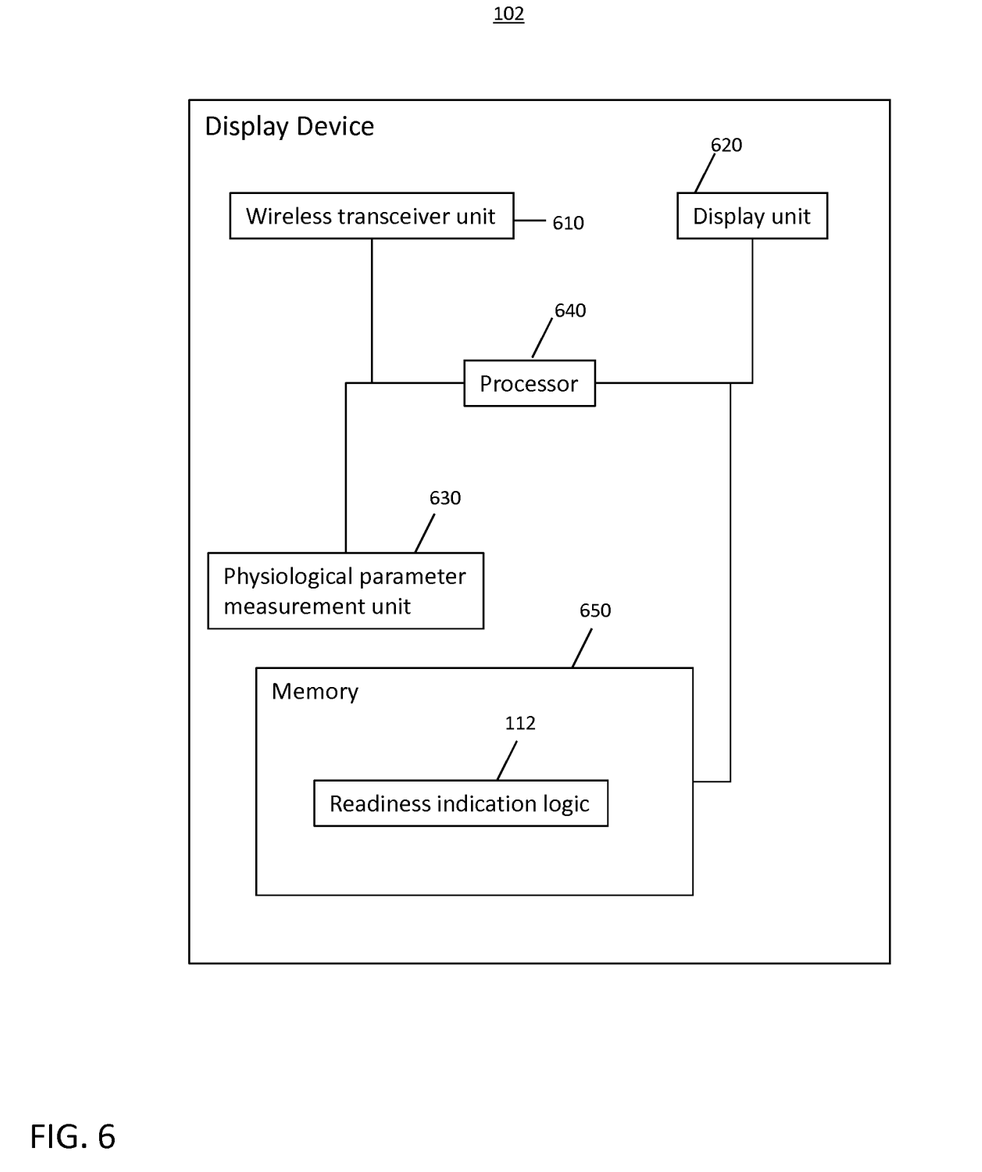
FIG. 6 shows an example block diagram of the display device that displays the exercise readiness to the user.

Reference is now made to FIG. 6. FIG. 6 shows a block diagram of the display device 102. The display device 102 has a wireless transceiver unit 610, a display unit 620, a physiological parameter measurement unit 630, a processor 640, and memory 650. The wireless transceiver unit 610 is configured to send and receive data wirelessly from other devices (e.g., devices 104(1)-104(n) and/or server 106). The wireless transceiver unit 610 may send and receive physiological data associated with a user, as described above. It should be appreciated that such wireless transmissions may be in accordance with known wireless technologies (e.g., Wi-Fi, Bluetooth, radio frequency transmissions, near field communication transmissions, etc.). The display unit 620 is configured to display information to a user. For example, as described above, the display device 102 may be a scale, and thus the display unit 620 of the display device 102 may be configured to display visually to a user data (e.g., physiological data such as weight, BMI, body fat percentage, heart rate, heart rate variability, bone density, etc.). The physiological parameter measurement unit 630 may comprise one or more sensors configured to measure physiological data of a user. For example, the physiological parameter measurement unit 630 may comprise force sensors to measure weight, impedance sensors to measure body fat percentage, heart rate sensors to measure heart rate and heart rate variability, etc. The wireless transceiver unit 610, the display unit 620 and the physiological parameter measurement unit are all connected (in communication) with the processor 640. The processor 640 is, for example, a microprocessor or microcontroller that is configured to execute program logic instructions (i.e., software) for carrying out various operations and tasks of the display device 102, as described above. For example, the processor 640 is configured to execute the readiness indication logic 112 stored in memory 650 to display an exercise readiness indication to a user. The functions of the processor 640 may be implemented by logic encoded in one or more tangible computer readable storage media or devices (e.g., storage devices, compact discs, digital video discs, flash memory drives, etc. and embedded logic such as an application specific integrated circuit (ASIC), digital signal processor instructions, software that is executed by a processor, etc.).

The memory 650 may comprise read only memory (ROM), random access memory (RAM), magnetic disk storage media devices, optical storage media devices, flash memory devices, electrical, optical, or other physical/tangible (non-transitory) memory storage devices. The memory 650 stores software instructions for the readiness indication logic 112. Thus, in general, the memory 650 may comprise one or more computer readable storage media (e.g., a memory storage device) encoded with software comprising computer executable instructions and when the software is executed (e.g., by the processor 640) it is operable to perform the operations described for the readiness indication logic 112, as described herein.

The readiness indication logic 112 may take any of a variety of forms, so as to be encoded in one or more tangible computer readable memory media or storage device for execution, such as a fixed logic or programmable logic (e.g., software/computer instructions executed by a processor), and the processor 640 may be an ASIC that comprises fixed digital logic or a combination thereof.

For example, the processor 640 may be embodied by digital logic gates in a fixed or programmable digital logic integrated circuit, which digital logic gates are configured to perform the readiness indication logic 112. In general, the readiness indication logic 112 may be embodied in one or more computer readable storage media encoded with software comprising computer executable instructions and when the software is executed operable to perform the operations described herein.

In summary, a method is described for providing an indicator to a user. The method comprises: at a display device, receiving information of a physiological measurement of the user; determining if the physiological measurement falls within a predetermined range of values; and displaying to the user an exercise readiness indication that represents a readiness state of the user to participate in an exercise activity based on the physiological measurement.

In addition, a system is described comprising: a physiological measurement device that is configured to measure a physiological measurement including at least one of a heart rate or heart rate variability or both; and a display device configured to: receive from the physiological measurement device information of the physiological measurement; determine if the physiological measurement falls within a predetermined range of values; and display to the user an exercise readiness indication that represents a readiness state of the user to participate in an exercise activity based on the physiological measurement.

Furthermore, one or more computer readable storage media is provided that is encoded with software comprising computer executable instructions and when the software is executed operable to: receive information of a physiological measurement of a user; determine if the physiological measurement falls within a predetermined range of values; and display to the user an exercise readiness indication that represents a readiness state of the user to participate in an exercise activity based on the physiological measurement.

The above description is intended by way of example only. Various modifications and structural changes may be made therein without departing from the scope of the concepts described herein and within the scope and range of equivalents of the claims.

What is claimed is:

1. An electronic apparatus comprising:
a wireless transceiver;
a physiological measurement apparatus comprising a sensor configured to obtain physiological measurements relating to a user;
a memory configured to record the physiological measurements relating to the user;
a display unit; and
a processor connected to each of the wireless transceiver, the physiological measurement apparatus, the memory, and the display unit, the processor configured to execute a plurality of instructions which are configured to, when executed, cause the electronic apparatus to:
perform an analysis of a plurality of previously recorded first physiological measurements relating to the user, the previously recorded first physiological measurements being taken on a respective first plurality of time periods, wherein at least one of the plurality of first physiological measurements relating to the user is obtained by the physiological measurement apparatus;
derive a user-specific range of acceptable values for one or more second physiological parameters based at least in part on said analysis;
receive a measurement of one of the one or more second physiological parameters relating to the user, the measurement being taken on a second time period via the physiological measurement apparatus, wherein the second time period is separate from the first plurality of time periods;
compare the measurement of the one of the one or more second physiological parameters relating to the user to the range of acceptable values therefor; and
cause the display unit to display an indication of a readiness level of the user such that:
when the measurement of the one of the one or more second physiological parameters relating to the user is within the range of acceptable values therefor, the indication comprising an indication of a positive physical readiness condition indicative that the user is in condition to perform a workout during the second time period;
when the measurement of the one or more second physiological parameters relating to the user is outside of the range of acceptable values, but less than a threshold amount stored in the memory, the indication comprising an indication of a non-optimal physical readiness condition indicative that the user may be in condition to perform a workout during the second time period; and
when the measurement of the one or more second physiological parameters relating to the user is outside of the range of acceptable values, and more than the threshold amount, the indication comprising an indication of a negative physical readiness condition indicative that the user is not in condition to begin a workout during the second time period.

2. The electronic apparatus of claim 1, wherein the indication of the readiness level of the user is displayed using one of a plurality of colors, wherein the display unit lights with the one color in order to provide the readiness indication, and wherein the one of the plurality of colors is:
   a first color when the measurement of the one of the one or more second physiological parameters relating to the user is within the range of acceptable values;
   a second color when the measurement of the one or more second physiological parameters relating to the user is outside of the range of acceptable values, but less than a threshold amount, the second color different from the first color; and
   a third color when the measurement of the one or more second physiological parameters relating to the user is outside of the range of acceptable values, and more than the threshold amount, the third color different from the first color and the second color.

3. The electronic apparatus of claim 1, wherein the physiological measurement apparatus comprises at least one of: a step count measuring device, a sleep measuring device, a heart rate measuring device, and an accelerometer.

4. A non-transitory computer readable apparatus comprising a plurality of executable instructions which are configured to when executed by a processor of an electronic apparatus, cause the processor to:
   receive a plurality of previously recorded first physiological measurements relating to a user, the previously recorded first physiological measurements being taken on a respective first plurality of time periods;
   perform an analysis of a plurality of the first physiological measurements and derive based at least in part on said analysis a user-specific range of acceptable values for one or more second physiological parameters;
   receive take a measurement via a sensor, the measurement of one of the one or more second physiological parameters relating to the user, the measurement taken on a second time period, the sensor provided by a physiological measurement apparatus, wherein the second time period is separate from the first plurality of time periods;
   receive from the sensor the measurement of the one of the one or more second physiological parameters relating to the user;
   compare the measurement of the one of the one or more second physiological parameters relating to the user to the range of acceptable values therefor; and
   based on the comparison, cause a display unit to display an indication of a readiness level of the user;
   wherein when the measurement of the one of the one or more second physiological parameters relating to the user is within the range of acceptable values therefor, the indication comprising an indication of a positive physical readiness condition indicative that the user is in condition to perform a workout during the second time period;
   wherein when the measurement of the one or more second physiological parameters relating to the user is outside of the range of acceptable values, but less than a threshold amount, the indication comprising an indication of a non-optimal physical readiness condition indicative that the user may possibly be in condition to perform a workout during the second time period; and
   wherein when the measurement of the one or more second physiological parameters relating to the user is outside of the range of acceptable values, and more than the threshold amount, the indication comprising an indication of a negative physical readiness condition indicative that the user is not in condition to begin a workout during the second time period.

5. The computer readable apparatus of claim 4, wherein the physiological measurement apparatus comprises at least one of: a step count measuring device, a sleep measuring device, a heart rate measuring device, and an accelerometer.

6. The computer readable apparatus of claim 4, wherein the electronic apparatus comprises a smart scale apparatus and the display unit is configured to display the indication of the readiness level of the user when the user is standing on or standing near the smart scale apparatus.

7. A method for providing an indicator to a user via an electronic apparatus, the method comprising:
   taking, via at least one sensor of a physiological measurement apparatus, a plurality of first physiological measurements relating to a user, the plurality of first physiological measurements being taken via the at least one sensor on respective first plurality of time periods;
   receiving the plurality of first physiological measurements relating to the user from the physiological measurement apparatus;
   analyzing the plurality of first physiological measurements relating to the user and deriving based at least in part on said analysis a user-specific range of acceptable values for one or more second physiological parameters;
   taking, via the at least one sensor of the physiological measurement apparatus, a measurement of one of the one or more second physiological parameters relating to the user, the measurement being taken on a second time period via a sensor of the physiological measurement apparatus, wherein the second time period is separate from the first plurality of time periods;
   receiving the measurement of one of the one or more second physiological parameters relating to the user from the physiological measurement apparatus,
   comparing the measurement of the one of the one or more second physiological parameters relating to the user to the range of acceptable values therefor;
   when the measurement of the one of the one or more second physiological parameters relating to the user is within the range of acceptable values therefor, causing a display unit to display an indication of a positive physical readiness condition indicative that the user is in condition to perform a workout during the second time period;
   when the measurement of the one or more second physiological parameters relating to the user is outside of the range of acceptable values, but less than a threshold amount, causing the unit to display an indication of a non-optimal physical readiness condition indicative that the user may only possibly be in condition to begin a workout during the second time period; and
   when the measurement of the one or more second physiological parameters relating to the user is outside of the range of acceptable values, and more than the threshold amount, causing the display unit to display an indication of a negative physical readiness condition indicative that the user is not in condition to begin a workout during the second time period.

8. The method of claim 7, wherein the first physiological measurement comprises a heart rate measurement metric, a heart rate variability measurement metric, or both.

9. The method of claim 7, wherein the indication that the user may begin a workout during the second time period comprises the display unit lighting up with a first color, the indication that the user may begin a workout during the second time period comprises the display unit lighting up with a second color that is different from the first color, and the indication that the user may not begin a workout during the second time period comprises the display unit lighting up with a third color that is different from the first color and the second color.

10. The method of claim 7, wherein the act of recording a plurality of first physiological measurements relating to a user further comprises at least one of:
  receiving the plurality of first physiological measurements from one or more devices in wireless communication with the display unit; and
  receiving the plurality of first physiological measurements by performing a measurement on the user.

11. The method of claim 7, wherein the physiological measurement apparatus comprises at least one of: a step count measuring device, a sleep measuring device; a heart rate measuring device, and an accelerometer.

12. The method of claim 7, wherein the electronic apparatus comprises a smart scale apparatus and the display unit is configured to display the indication when the user is standing on or standing near the smart scale apparatus.

* * * * *